United States Patent [19]

Maresch et al.

[11] Patent Number: 5,554,362
[45] Date of Patent: Sep. 10, 1996

[54] COMPOSITION AND PROCESS FOR THE PERMANENT SHAPING OF HAIR

[75] Inventors: Gerhard Maresch, Darmstadt, Germany; Hans-Jürgen Braun, Ueberstorf, Switzerland

[73] Assignee: Wella Aktiengesellschaft, Darmstadt, Germany

[21] Appl. No.: 246,112

[22] Filed: May 19, 1994

[30] Foreign Application Priority Data

May 19, 1993 [DE] Germany .......................... 43 16 750.0

[51] Int. Cl.$^6$ .............................. H61K 7/09; H61K 7/06
[52] U.S. Cl. ...................... 424/70.51; 424/70.2; 132/204
[58] Field of Search .............................. 424/71, 72, 70.2, 424/70.51; 132/204

[56] References Cited

U.S. PATENT DOCUMENTS

| | | | |
|---|---|---|---|
| 2,615,828 | 10/1952 | Haefele | 424/72 |
| 2,719,813 | 10/1955 | Haefela | 424/72 |
| 2,719,814 | 10/1955 | Haefele | 424/72 |
| 2,828,208 | 3/1958 | Anagnostopoulos | 99/4 |
| 4,898,726 | 2/1990 | Beste | 424/72 |

FOREIGN PATENT DOCUMENTS 797167   6/1958   United Kingdom ..................... 424/71

*Primary Examiner*—Thurman K. Page
*Assistant Examiner*—Sally Gardner
*Attorney, Agent, or Firm*—Michael J. Striker

[57] ABSTRACT

The hair shaping composition for permanent shaping of hair has a pH of from 6 to 9 and contains one or more conventional cosmetic additives, which can include water; perfume oil and/or a surface active compound, and from 5 to 25 percent by weight of 2-hydroxy-3-mercaptopropionic acid and/or its salts as active keratin-reducing agent. Preferably the 2-hydroxy-3-mercaptopropionic acid and/or its salts are the only keratin-reducing components in the composition. The method for permanent shaping of hair using this hair shaping composition allows a ready and uniform shaping of the hair without allergic or sensitizing reaction.

8 Claims, No Drawings

COMPOSITION AND PROCESS FOR THE PERMANENT SHAPING OF HAIR

BACKGROUND OF THE INVENTION

The present invention relates to a composition for permanent shaping of hair which contains 2-hydroxy-3-mercaptopropionic acid as an effective keratin-reducing ingredient and a process for permanent shaping of hair using this composition.

The well known classic method for performing the permanent shaping of hair consists of opening the disulfide bonds of the hair keratin with the aid of an agent (hair shaping composition) which contains a reducing agent, putting the hair in the desired form or shape and subsequently reforming the disulfide bridges again using an agent containing an oxidizing agent (fixing composition).

Sulfite, thioglycolic acid, thiolactic acid, 3-mercaptopropionic acid, mercaptocarboxylic acid ester, Cysteine and its derivatives or Cysteamine and its derivatives are used as reducing agents in the method.

It is known that mercaptocarbonic acid ester, for example thioglycolic acid glycerin ester, are not satisfactory in regard to their skin compatibility and their sensitizing properties, while the thioglycolic acid has a high toxicity in comparison to Cysteine.

SUMMARY OF THE INVENTION

It is an object of the present invention to provide a new keratin-reducing composition which is as natural as possible (which means that it occurs as a metabolism product in humans), which has good skin compatibility properties, a reduced sensitization risk, a lower toxicity and a good biodegradability.

Surprisingly it has now been found that an efficacious shaping of the hair is possible using a hair shaping composition containing 2-hydroxy-3-mercaptopropionic acid and its salts which have good physiological compatibility and reduced sensitizing risk.

The composition according to the invention for permanent shaping of hair contains 2-hydroxy-3-mercaptopropionic acid and/or its salts as keratin-reducing agent.

The salts of 2-hydroxy-3-mercaptopropionic acid which are preferred according to the invention include the alkali metal salts, the ammonium salt and the monoethanol amine salts of 2-hydroxy-3-mercaptopropionic acid. The ammonium salt and the monoethanol amine salts are particularly preferred.

Of course it is possible to use the 2-hydroxy-3-mercaptopropionic acid and/or its salts together with other keratin-reducing materials—for example thioglycolic acid, thiolactic acid, 3-mercaptopropionic acid, Cysteine or its derivatives or Cysteamine or its derivatives, however the use of the 2-hydroxy-3-mercaptopropionic acid and/or its salts as the effective keratin-reducing material or agent (that means without addition of other keratin-reducing agents or materials) is particularly preferred.

The 2-hydroxy-3-mercaptopropionic acid and/or its salts in the ready hair shaping composition according to the invention are present in an amount of 5 to 25 percent by weight, advantageously 8 to 20 percent by weight.

The ready hair shaping agent according to the invention has a pH of 6 to 9, advantageously 6.5 to 8.5

The permanent shaping agent can be in the form of an aqueous solution or an emulsion and also in thickened form in aqueous media, particularly as a gel, cream or paste.

Understandably conventional cosmetic additives can be used in the hair shaping composition, e.g. thickeners, such as kaolin, bentonite, fatty acids, higher fatty alcohols, starch, polyacrylic acid and its derivatives, cellulose derivatives, alginate, vaseline or paraffin oil; wetting agent or emulsifier from the classes of anioinic, cationic, amphoteric or nonionic surface active compounds, particularly fatty alcohol sulfates, fatty alcohol ether sulfates, alkyl sulfonates, alkylbenzene sulfates, quaternary ammonium salts, alkyl betaine, ethoxylated alkylphenols, fatty acid alkanol amides or ethoxylated fatty acid esters; tubidity-inducing agents, such as polyethylene glycol ester; or alcohols, especially ethanol, propanol, isopropanol or glycerin; dissolving intermediaries stabilizers; buffer substances; perfume oil; dyes and hair conditioning and hair care components, such as cationic polymers, lanolin derivates, cholesterin, pantothenic acids or betaine. The cosmetic additives or ingredients are present in amounts sufficient to accomplish their purpose, for example the wetting agents and emulsifiers are present as 0.2 to 30 percent by weight of the hair shaping composition, while the thickeners are present in an amount of 0.5 to 20 percent by weight.

A promoter substance, a so-called swelling and penetrating agent, such as dipropyleneglycolmonomethyl ether, 2-pyrrolidone or imidazolidin-2-one, can be added to the hair shaping composition in an amount of from 2 to 30 percent by weight. Dithiocompounds, particularly dithiodiglycolic acid, dithiodilactic acid or their salts, can be added to the hair shaping composition to avoid over curling of the hair.

A hair shaping composition which is universally effective for any type of hair structure can be provided by variation of the pH of the hair shaping composition, if necessary with additional heating. The agent causes an elastic permanent, uniform shaping of the hair from the hair roots to the hair tips.

The permanent shaping of the hair using the hair shaping composition according to the invention is performed by a process in which before or after one brings the hair into the desired shape, it is treated with the hair shaping agent, rinsed with water, then subjected to an oxidative after-treatment, rinsed with water, if necessary put in a water wave and then dried. This process is characterized in that the hair shaping composition according to the invention is used as the hair shaping agent.

First the hair is washed with a shampoo and after that rinsed with water. Subsequently the hand towel dried hair can be divided into individual strands and wound on curlers with a diameter of 5 to 30 millimeters, advantageously 5 to 15 millimeters. Then the hair is treated with an amount of hair shaping agent according to the invention which is sufficient for hair shaping, advantageously from 60 to 120 grams.

After an acting time sufficient for the permanent shaping of the hair, which amounts to from 5 to 30 minutes depending on the application temperature, the hair properties, the pH value and the shaping effectiveness of the shaping agent (10 to 30 minutes without heating; 5 to 20 minutes with heating), the hair is rinsed with water and then subjected to an oxidative after-treatment ("fixed"). The oxidative after-treatment agent is used in an amount of 80 to 100 grams according to hair feel.

Any oxidative after-treatment agent used up to now in oxidative after-treatments can be used in the oxidative after-treatment according to the invention. Examples of a suitable oxidative after-treatment agent include potassium bromate, sodium bromate, sodium perborate, urea peroxide and hydrogen peroxide. The concentration of the oxidizing agent differs depending on the application time (usually 5 to 15 minutes) and the application temperature. Normally the oxidizing agent present in the commercially available aqueous oxidative after-treatment composition amounts to from 0.5 to 10 percent by weight. The means for oxidative after-treatment can understandably contain an additional substance, for example wetting agent, hair care material such as cationic active polymers, weak acids, buffer substances or peroxide stabilizing agents and can be in the form of an aqueous solution, an emulsion as well as in thickened form in aqueous media, especially in a cream, gel or paste.

Subsequently the curlers are removed. As the case may require, the curled hair can now be subjected once again to an oxidative after-treatment. Then the hair is rinsed, if necessary put in a water wave and subsequently dried.

The subsequent examples illustrate the invention, but should not to be considered limiting for the claims appended hereinbelow.

EXAMPLES

Example 1

Hair Shaping Composition for Dyed Hair

| | |
|---|---|
| 10.0 g | 2-hydroxy-3-mercaptopropionic acid |
| 6.1 g | ammonia (25% aqueous solution) |
| 2.0 g | ammonium hydrogen carbonate |
| 2.0 g | isopropanol |
| 1.0 g | isooctylphenol, ethoxylated with 10 mole of ethylene oxide |
| 1.0 g | poly(dimethyldiallyl ammonium chloride) |
| 0.3 g | perfume oil |
| 0.1 g | vinyl pyrrolidone/styrene mixed polymerizate (Antara$^R$ 430 of GAF Corp.; New York /USA) |
| 77.5 g | water |
| 100.0 g | |

The pH value of this composition amounts to 8.0.

Hair damaged by a dyeing process is washed with a shampoo, rubbed and wound on curlers with a diameter of 8 millimeters. Subsequently the above described hair shaping agent is distributed on the curved hair uniformly. Then the hair is covered with a plastic cover and heated for 10 minutes under a drying hood at a temperature of 40° C. Subsequently the cover is removed, the hair is rinsed with water and oxidatively after-treated with 100 grams of a 3 percent aqueous solution of hydrogen peroxide. After removal of the curlers the hair is rinsed with fresh water, put in a water wave and dried.

A uniform elastic permanent shaping of the hair is obtained as a result of the treatment with the hair shaping composition according to the invention. EXAMPLE 2

Hair Shaping Composition for Normal Hair

| | |
|---|---|
| 16.0 g | 2-hydroxy-3-mercaptopropionic acid |
| 8.9 g | ammonia (25% aqueous solution) |
| 5.0 g | ammonium hydrogen carbonate |
| 4.0 g | urea |
| 2.4 g | monoethanolamine |
| 1.5 g | isooctylphenol, ethoxylated with 10 mole of ethylene oxide |
| 0.5 g | poly(dimethyldiallylammonium chloride) |
| 0.5 g | perfume oil |
| 0.1 g | vinyl pyrrolidone/styrene mixed polymerizate (Antara$^R$ 430 of GAF Corp.; New York /USA) |
| 61.1 g | water |
| 100.0 g | |

The pH value of this composition amounts to 8.4.

Normal undamaged hair is washed with a shampoo, rubbed and wound on curlers with a diameter of 6 millimeters. Subsequently the above described hair shaping agent is moistened on the curved hair. After an acting time on the hair of 15 minutes the hair is rinsed with water and then subsequently treated with 80 grams of a 3 percent aqueous hydrogen peroxide solution. After removal of the curlers the hair is rinsed with fresh water, put in a water wave and dried.

The hair so treated has a uniform and vivacious curl.

EXAMPLE 3

Hair Shaping Composition for Normal Hair and Difficult-to-Shape Hair

| | |
|---|---|
| 3.0 g | 2-hydroxy-3-mercaptopropionic acid |
| 15.0 g | Cysteine hydrochloride |
| 11.0 g | ammonia (25% aqueous solution) |
| 1.5 g | isooctylphenol, ethoxylated with 10 mole of ethylene oxide |
| 0.5 g | poly(dimethyldiallylammonium chloride) |
| 0.5 g | perfume oil |
| 0.1 g | vinyl pyrrolidone/styrene mixed polymerizate (Antara$^R$ 430 of GAF Corp.; New York /USA) |
| 68.4 g | water |
| 100.0 g | |

The pH value of this composition amounts to 8.7.

The hair is treated in the same manner as in example 2 however the time the hair shaping agent is allowed to act on the hair is about 20 minutes.

This treatment provides a uniform natural shaping of the hair from the hair roots to the hair tips.

While the invention has been illustrated and described as embodied in a composition and process for permanent shaping of hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Hair shaping composition for permanent shaping of hair having a pH of from 6 to 9 and containing water; from 5 to 25 percent by weight of at least one keratin-reducing agent selected from the group consisting of 2-hydroxy-3-mercaptopropionic acid and ammonium, alkali metal and monoethanol amine salts of said 2-hydroxy-3-mercaptopropionic acid; and at least one cosmetic additive selected from the group consisting of kaolin, bentonite, fatty acids, fatty alcohols, starch, polyacrylic acid, cellulose, alginate, vaseline, paraffin oil; anionic, cationic, amphoteric and nonionic surface active compounds; turbidity-inducing agents; dissolving intermediaries; alcohols; stabilizers; buffers; perfume oil; dyes; cationic polymers, lanolin, cholesterin and pantothenic acid.

2. Hair shaping composition as defined in claim 1, containing no keratin-reducing means other than said at least one keratin-reducing agent.

3. Hair shaping composition as defined in claim 1, containing at least one additional keratin-reducing agent besides said at least one keratin-reducing agent, wherein said at least one additional keratin-reducing agent is selected from the group consisting of thioglycolic acid, thiolactic acid, 3-mercaptopropionic acid, Cysteine and Cysteamine.

4. Hair shaping composition as defined in claim 1, in the form of an aqueous solution, a gel, a cream or a paste.

5. Hair shaping composition as defined in claim 1, wherein said surface active compounds are selected from the group consisting of fatty alcohol sulfates, fatty alcohol ether sulfates, alkyl sulfonates, alkylbenzene sulfates, quaternary ammonium salts, alkyl betaine, ethoxylated alkylphenols, fatty acid alkanol amides and ethoxylated fatty acid esters.

6. Hair shaping composition as defined in claim 1, wherein said surface active compounds are present in amounts from 0.2 to 30 percent by weight.

7. Method for permanent shaping of hair comprising the steps of bringing the hair into a shape, treating the hair with a hair shaping composition having a pH of from 6 to 9 and containing from 5 to 25% by weight of at least one keratin-reducing agent selected from the group consisting of 2-hydroxy-3-mercapto-propionic acid and ammonium, alkali metal and monoethanol amine salts of said 2-hydroxy-3-mercaptopropionic acid; allowing the hair shaping composition to act on the hair for from 5 to 30 minutes; rinsing the hair with water; after the rinsing of the hair with the water, performing an oxidative after-treatment with from 80 to 100 grams of an oxidative after-treatment agent selected from the group consisting of potassium bromate, sodium bromate, sodium perborate, urea peroxide and hydrogen peroxide; after the oxidative after-treatment, rinsing the hair again with water and then drying the hair.

8. Method as defined in claim 7, wherein from 60 to 120 grams of said hair shaping composition is applied to the hair during the treating of the hair with the hair shaping composition.

* * * * *